United States Patent [19]

Owen et al.

[11] Patent Number: 4,834,949
[45] Date of Patent: May 30, 1989

[54] MULTISTAGE SYSTEM FOR CONVERTING OLEFINS TO HEAVIER HYDROCARBONS

[75] Inventors: Hartley Owen, Belle Mead; Bernard S. Wright, East Windsor, both of N.J.

[73] Assignee: Mobil Oil Corporation, New York, N.Y.

[21] Appl. No.: 118,925

[22] Filed: Nov. 10, 1987

Related U.S. Application Data

[63] Continuation-in-part of Ser. No. 775,907, Sep. 13, 1985.

[30] Foreign Application Priority Data

| Jun. 18, 1986 [Au] | Australia | 58819-86 |
| Aug. 28, 1986 [Ca] | Canada | 517114 |
| Sept. 2, 1986 [Ep] | European Pat. Off | 86306786.4 |
| Sept. 1, 1986 [Ja] | Japan | 61-203910 |
| Sept. 5, 1986 [Za] | South Africa | 86-6711 |

[51] Int. Cl.⁴ ............................................. B01J 8/04
[52] U.S. Cl. .................................. 422/190; 422/142; 422/234; 422/235
[58] Field of Search ............... 422/190, 234, 235, 142

[56] References Cited

U.S. PATENT DOCUMENTS

| 4,433,185 | 2/1984 | Tabak | 585/312 |
| 4,487,985 | 12/1984 | Tabak | 585/517 |
| 4,542,247 | 9/1985 | Chang et al. | 585/254 |
| 4,543,435 | 9/1985 | Gould et al. | 585/330 |
| 4,547,602 | 10/1985 | Tabak | 585/314 |
| 4,579,999 | 4/1986 | Gould et al. | 585/312 |

Primary Examiner—Asok Pal
Attorney, Agent, or Firm—Alexander J. McKillop; Charles J. Speciale; Lowell G. Wise

[57] ABSTRACT

A multistage reactor system and operating technique for converting ethene-rich olefinic feedstock to heavier hydrocarbons, particularly gasoline and distillate range products. By employing low temperature and high temperature separators, an economic recycle is provided for each stage.

5 Claims, 2 Drawing Sheets

4,834,949

MULTISTAGE SYSTEM FOR CONVERTING OLEFINS TO HEAVIER HYDROCARBONS

REFERENCE TO COPENDING APPLICATION

This application is a continuation-in-part of U.S. patent application Ser. No. 775,907, filed 13 Sept. 1985, incorporated herein by reference.

FIELD OF THE INVENTION

This invention relates to a multistage reactor system and unit operations for upgrading light olefins to liquid hydrocarbons. In particular it provides a continuous technique for producing distillate range fuel products by oligomerizing ethene-rich olefinic feedstock to produce a major amount of distillate product for use as diesel fuel or the like.

BACKGROUND OF THE INVENTION

Recent developments in zeolite catalysis and hydrocarbon conversion processes have created interest in utilizing olefinic feedstocks, for producing $C_5^+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$–$C_5$ alkenes. In U.S. Pat. Nos. 3,960,978 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5^+$ aliphatic and aromatic hydrocarbons. Olefinic gasoline can be produced in good yield by the MOGD process and may be recovered as a product or fed to a low severity reactor system for further conversion to distillate-range products. Distillate mode operation can be employed to maximize production of $C_{10}^+$ aliphatics by reacting the lower olefins at high pressure and moderate temperature. Operating details for typical MOGD units are disclosed in U.S. Pat. Nos. 4,456,779; 4,497,968 (Owen et al) and No. 4,433,185 (Tabak), incorporated herein by reference.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the low severity distillate mode conditions do not convert a major fraction of ethene. While propene, butene-1 and others may be converted to the extent of 50 to 95% in the distillate mode, only about 10 to 30% of the ethylene component will be converted.

SUMMARY OF THE INVENTION

A continuous multi-stage catalytic technique has been found for converting ethene-rich lower olefinic feedstock to heavier liquid hydrocarbon product. Apparatus an operatively connected multistage reactor means are provided for contacting ethene-rich feedstock at elevated temperature and moderate pressure in a primary stage high severity reaction zone with shape selective medium pore zeolite oligomerization catalyst to convert at least a portion of the lower olefinic components to intermediate olefinic hydrocarbons. Means are provided for cooling primary stage oligomerization reaction effluent from the high severity reaction zone to condense at least a portion of the intermediate hydrocarbons, separating the cooled and partially condensed high severity reactor effluent stream in a primary phase separation zone into a light gas phase stream comprising unreacted light olefin and a condensed liquid intermediate hydrocarbon stream. Advantageously in fixed bed reactors, by recycling a major portion of the primary gas stream to the primary stage reaction zone, unreacted ethene and other gases may be further converted or provide reaction diluent. In other process configurations, it may be desirable to withdraw such light gas from a single pass fluid bed stage. By pressurizing and contacting the intermediate liquid stream from the primary stage with shape selective medium pore zeolite oligomerization catalyst in a secondary stage distillate mode catalytic reactor system at elevated temperature and high pressure, a heavier hydrocarbon effluent stream is produced comprising distillate and lighter hydrocarbons.

An important aspect of this invention regards a novel technique for connecting the phase separation units in the primary and secondary stages for operating advantages. Recycle for the secondary stage is provided by flashing and cooling the secondary stage effluent stream for separation in a secondary phase separation zone to recover a distillate-rich product stream and a lighter hydrocarbon vapor stream comprising intermediate hydrocarbons and recycling at least a portion of the recovered secondary stage vapor stream for combining in the primary stage effluent prior to phase separation.

DESCRIPTION OF PREFERRED EMBODIMENTS

Figure 1:
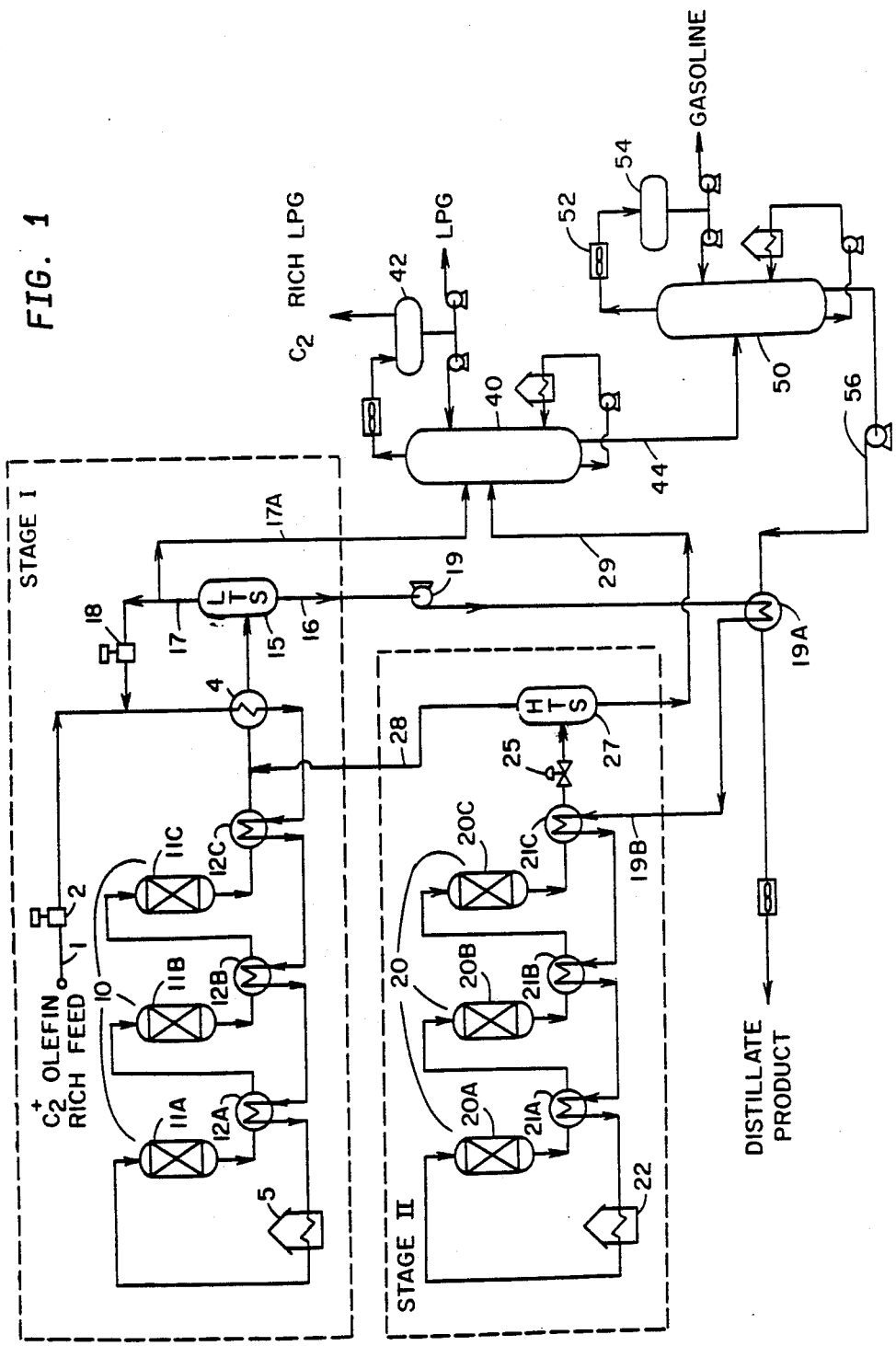
FIG. 1 is a process flow sheet depicting the invention.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion includes the medium pore (i.e., about 5-7 angstroms) shape selective crystalline aluminosilicate zeolites having a silica to alumina ratio of about 20:1 or greater, a constraint index of about 1-12, and acid cracking activity (alpha value) of about 10-200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); 4,046,339 (ZSM-38); and 4,375,573 (ZSM-48). The disclosures of these patents are incorporated herein by reference.

While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica clay and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IB, IIB, IIIB, VA, VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent Application Ser. No. 893,522, filed 4 Aug. 1986 by Garwood et al, incorporated herein by reference.

Catalyst versatility permits the same or similar types of zeolite to be used in both the primary stage and distillate mode secondary oligomerization stage. While it is within the inventive concept to employ substantially different catalysts in these stages, it is advantageous to employ a standard ZSM-5 having a silica alumina molar ratio of 70:1.

A suitable catalyst for each fixed bed operation may consist essentially of ZSM-5 zeolite with 35 wt. % alumina binder in the form of cyclindrical extrudates of about 1-5 mm diameter. These zeolites may be employed in their acid forms or ion exchanged with suitable metal cations, such as Ni, Co and/or other metals of Periodic Groups III to VIII. Other catalysts which may be employed for converting lower olefins include the borosilicate, ferrosilicate, "silicalite" and/or synthetic mordenite materials.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

The preferred feedstock comprises at least 25 mole % ethene and may consist essentially of $C_2$-$C_6$ olefins, such normal mono-olefins and isomers thereof.

Stage I—Primary Stage Reactor Operation

The term higher severity, as employed herein, refers to the combination of materials and conditions effective to convert a major amount (more than 50%) of ethene. This degree of reaction severity may be achieved by elevated temperature, catalyst activity, etc. in a known manner. In FIG. 1 of the drawing, ethene-containing olefinic feedstock is supplied to the plant through fluid conduit 1 under steady stream conditions. This $C_2^+$ feedstream is pressurized by compressor 2 and then sequentially heated by passing through process heat exchange units 4, 12 and furnace 5 to achieve the temperature for catalytic conversion in a first fixed bed reactor subsystem 10, including plural reactor vessels 11A, B, C. The reactor sub-system section shown consists of three downflow fixed bed, series reactors on line with heat exchanger cooling means 12 A, B, C between reactors and following the subsystem. The reactor configuration allows for any reactor to be in any position, A, B or C. The reactor in position A has the most aged catalyst and the reactor in position C has freshly regenerated catalyst. As will be described later, the primary stage reactor may also be operated as a fluidized bed catalytic stage, employing one or more reactor vessels.

The cooled reactor effluent from exchanger 4 is first separated in a primary phase low temperature separator unit (LTS) 15 is to provide a condensed $C_5^+$ rich hydrocarbon liquid stream 16 and a primary light gas stream 17 comprising $C_2$-$C_4$ aliphatic hydrocarbons, along with ethene or other unreacted gaseous components which might be present in the feedstock, such as hydrogen, carbon oxides, methane, nitrogen or other inert gases. A major portion of this light gas stream is repressurized by compressor unit 18 for recycle with fresh feedstock from compressor 2.

A typical higher severity multi-zone reactor system employs cooling, whereby the reaction exotherm can be carefully controlled to prevent excessive temperature above the normal moderate range of about 260° to 370°

C. Advantageously, the maximum temperature differential across any one reactor is about 30° C. and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a liquid stream to vaporize liquid hydrocarbons. Optional heat exchangers may recover heat from the effluent stream prior to fractionation. It is preferred to operate the high severity reactors at moderate pressure of about 1500 to 2900 kPa (200–400 psig), with a minimum olefin partial pressure of about 1200 kPa at the reactor system inlet.

The primary reactor system may contain multiple downflow adiabatic catalytic zones in each reactor vessel. The weight hourly space velocity (WHSV, based on total fresh feedstock) is about 0.1–2 LHSV. In this mode the molar recycle ratio for light gas is at least equimolar, based on total olefins in the fresh feedstock. The preferred molar ratio of recycle to fresh feedstock olefin is at least 2:1.

Stage II—Distillate Mode Oligomerization Reactor Operation

The secondary distillate production stage provides catalytic oligomerization reactor means containing medium pore shape selective zeolite oligomerization catalyst for converting lower and intermediate range olefinic hydrocarbons from the Stage I to liquid hydrocarbons comprising a major amount of distillate. Process stream 16, preferably comprising at least 75 mole % $C_5$ to $C_9$ aliphatic hydrocarbons, is pressurized for a substantially different process condition by pump means 19, operatively connected to provide a fluid handling system between Stages I and II. The intermediate liquid stream is preheated by indirect heat exchange with distillate product in exchanger 19A and passed to the Stage II subsystem at a pressure of at least about 4000 kPa, preferably about 4225 to 7000 kPa (600 to 1000 psig).

A typical distillate mode secondary stage reactor system 20 is depicted. A plural reactor system may be employed with inter-reactor cooling, whereby the reaction exotherm can be carefully controlled to prevent excessive temperature above the normal moderate range of about 190° to 315° (375°–600° F.). The olefinic intermediate stream comprising the $C_5$+ hydrocarbons is introduced through conduit 19B and carried by a series of conduits through heat exchangers 21A, B, C and furnace 22 where the intermediate stream is heated to reaction temperature. The olefinic stream is then carried sequentially through a series of zeolite beds 20A, B, C wherein a major portion of the olefin content is converted to heavier distillate constituents. Advantageously, the maximum temperature differential across only one reactor is about 30° C. (T 50° F.) and the space velocity (LHSV based on olefin feed) is about 0.5 to 1.5. The heat exchangers 21A and 21B provide inter-reactor cooling and 21C further reduces the effluent. After flashing by means of pressure reduction valve 25, the Stage II effluent is passed to secondary high temperature phase separator means 27.

This HTS unit is operated in a manner to recover the major amount of $C_{10}$+ hydrocarbons, while vaporizing light and intermediate ($C_9$−) hydrocarbons at a pressure below 4000 kPa and temperature at least 100° C. higher than LTS unit 15. This secondary vapor stream is recycled to Stage I via conduit 28. Advantageously, the HTS unit is operated at a pressure slightly above the Stage I effluent stream (e.g. about 3000 to 3500 kPa), with a recycle control system to maintain the desired pressure and flow rates.

Preferably, the secondary stage reactor conditions are optimized to produce heavy liquid hydrocarbons having a normal boiling above 165° C. (330° F.). A typical secondary stage HZSM-5 fixed bed reactor system may be operated at about 0.5 to 2 liquid hourly space velocity (based on total olefins fed to reactors), temperature of 230° C. (450° F.) (SOC) to 315° C. (600° F.) (EOC) and a total pressure of 4225 kPa (600 psig), with a minimum olefin partial pressure at the inlet of about 1100 kPa (160 psig).

Product fractionation is achieved outside the recycle loops by passing a gas phase slip stream 17A and distillate-rich liquid stream 29 to a debutanizer tower 40 where $C_3$–$C_4$ LPG product is recovered from overhead condenser separator 42 and $C_2$− of gas containing some unreacted ethene and a small amount of $C_4$− hydrocarbons is recovered. The $C_5$+ liquid bottoms stream 44 is passed to product splitter tower 50 where $C_5$–$C_9$ raw gasoline product is recovered from the overhead condenser 52 and accumulator 54 and the raw distillate product is recovered as a $C_{10}$+ bottoms stream via conduit 56 and exchanger 19A. Typical product fractionation systems are described in U.S. Pat. Nos. 4,456,779 and 4,504,693 (Owen et al).

It is within the inventive concept to cascade a major amount of $C_5$+ hydrocarbons from the primary stage into the distillate mode reactor. This will optimize the process and will maximize distillate production by polymerizing gasoline boiling range components. Because the primary stage is operated at a pressure level of about 200–400 psig (1500–2900 kPa), the compression requirements are efficient. Also, common separators are employed for both stages to effect preliminary product separation and provide recycle economically. In the prior art, a deethanizer and debutanizer is used to supply LPG recycle to one or both stages. Usually prior product fractionation is within the recycle loop for both stages, whereas in the present process the product fraction is outside the recycle loop. Consequently the new process will have both a lower capital investment and operating cost than that for prior systems.

Fluidized Bed Reactor Operation

Figure 2:
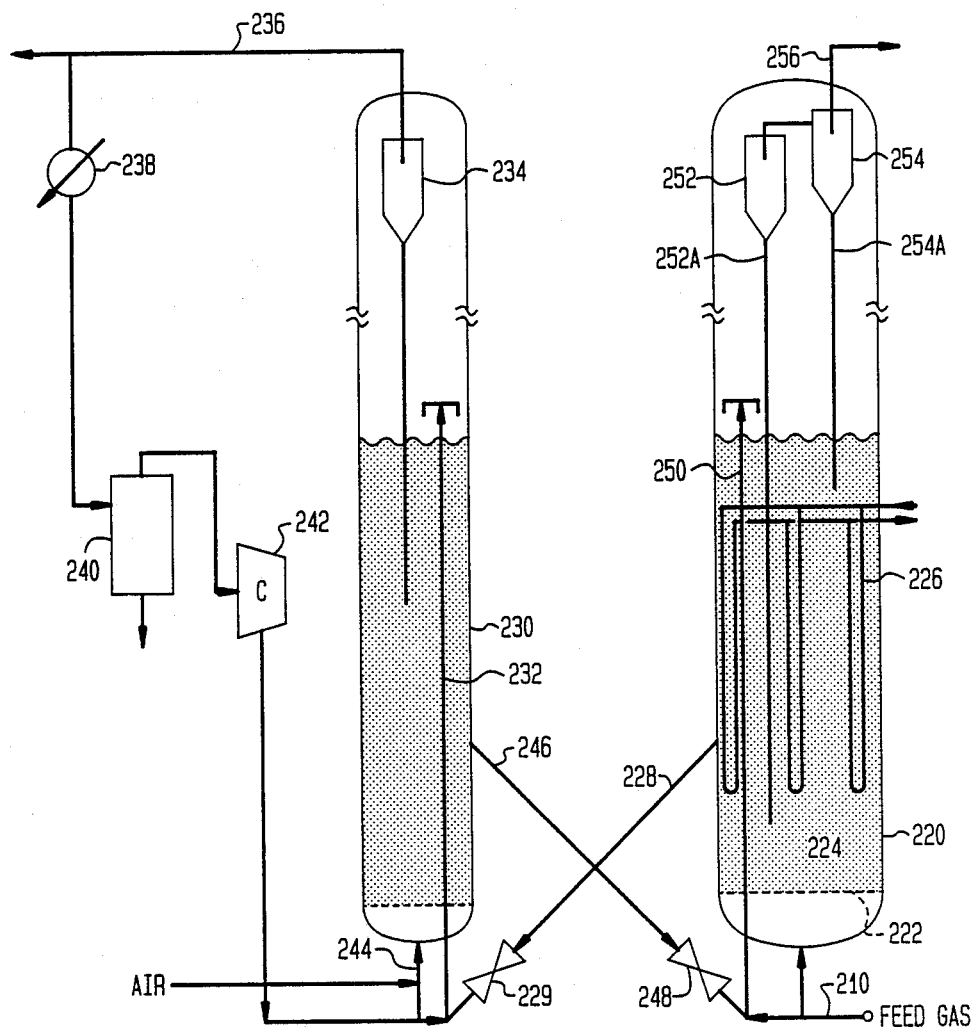
FIG. 2 is a vertical cross-section view of an alternative design primary stage fluidized bed reactor subsystem suitable for use in the present invention.

Referring to FIG. 2 of the drawing, a suitable primary stage fluidized bed oligomerization reactor unit is depicted employing a temperature-controlled catalyst zone with indirect heat exchange and/or adjustable gas quench, whereby the reaction exotherm can be carefully controlled to prevent excessive temperature above the usual operating range of about 260° C. to 430° C., preferably at average reactor temperature of 300° C. to 400° C. Energy conservation in the system may utilize at least a portion of the reactor exotherm heat value by exchanging hot reactor effluent with feedstock and/or recycle streams. Optional heat exchangers may recover heat from the effluent stream prior to fractionation. Part or all of the reaction heat can be removed from the reactor without using the indirect heat exchange tubes by using cold feed, whereby reactor temperature can be controlled by adjusting feed temperature. The internal heat exchange tubes can still be used as internal baffles which lower reactor hydraulic diameter, and axial and radial mixing. The use of a fluid-bed reactor offers several advantages over a fixed-bed reactor. Due to continuous catalyst regeneration, fluid-bed reactor operation will not be adversely affected by oxygenate, sulfur and/or nitrogen containing contaminants presented in FCC light gas.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

The oligomerization reaction severity conditions can be controlled to optimize yield of $C_5$-$C_9$ aliphatic hydrocarbons. It is understood that aromatic and light paraffin production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an average alpha value of about 10 to 20.

Reaction temperatures and contact time are also significant factors in determining the reaction severity, and the process parameters are followed to give a substantially steady state condition wherein the reaction severity index (R.I.) is maintained within the limits which yield a desired weight ratio of alkane to alkene produced in the reaction zone. This index may vary from about 0.1 to 7:1, in the substantial absence of $C_3+$ alkanes; but, it is preferred to operate the steady state fluidized bed unit to hold the R.I. at about 0.2 to 5:1. While reaction severity is advantageously determined by the weight ratio of propane:propene in the gaseous phase, it may also be measured by the analogous ratios of butanes:butenes, pentanes:pentenes (C.I.5), or the average of total reactor effluent alkanes:alkenes in the $C_3$-$C_5$ range. Accordingly, the product C5 ratio may be a preferred measure of reaction severity conditions, especially with mixed aliphatic feedstock containing $C_3$-$C_4$ alkanes.

The use of fluidized bed catalysis permits the conversion system to be operated at low pressure drop. Another important advantage is the close temperature control that is made possible by turbulent regime operation, wherein the uniformity of conversion temperature can be maintained within close tolerances, often less than 10° C. Except for a small zone adjacent the bottom gas inlet, the midpoint measurement is representative of the entire bed, due to the thorough mixing achieved.

In a typical process, the olefinic feedstock is converted in a catalytic reactor under oligomerization conditions and moderate pressure (i.e.—400 to 2500 kPa) to produce a predominantly liquid product consisting essentially of $C_5+$ hydrocarbons rich in gasoline-range olefins and essentially free of aromatics.

Referring now to FIG. 2, feed gas rich in lower olefins passes under pressure through conduit 210, with the main flow being directed through the bottom inlet of reactor vessel 220 for distribution through grid plate 222 into the fluidization zone 224. Here the feed gas contacts the turbulent bed of finely divided catalyst particles. Reactor vessel 210 is shown provided with heat exchange tubes 226, which may be arranged as several separate heat exchange tube bundles so that temperature control can be separately exercised over different portions of the fluid catalyst bed. The bottoms of the tubes are spaced above feed distributor grid 222 sufficiently to be free of jet action by the charged feed through the small diameter holes in the grid. Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 228 is provided for withdrawing catalyst from above bed 224 and passed for catalyst regeneration in vessel 230 via control valve 229. The partially deactivated catalyst is oxidatively regenerated by controlled contact with air or other regeneration gas at elevated temperature in a fluidized regeneration zone to remove carbonaceous deposits and restore acid activity. The catalyst particles are entrained in a lift gas and transported via riser tube 232 to a top portion of vessel 230. Air is distributed at the bottom of the bed to effect fluidization, with oxidation byproducts being carried out of the regeneration zone through cyclone separator 234, which returns any entrained solids to the bed. Flue gas is withdrawn via top conduit 236 for disposal; however, a portion of the flue gas may be recirculated via heat exchanger 238, separator 240, and compressor 242 for return to the vessel with fresh oxidation gas via line 244 and as lift gas for the catalyst in riser 232.

Regenerated catalyst is passed to the main reactor 220 through conduit 46 provided with flow control valve 248. The regenerated catalyst may be lifted to the catalyst bed with pressurized feed gas through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 252, 254 are provided with diplegs 252A, 254A to return any entrained catalyst fines to the lower bed. These separators are positioned in an upper portion of the reactor vessel comprising dispersed catalyst phase 224. Filters, such as sintered metal plate filters, can be used alone or conjunction with cyclones.

The product effluent separated from catalyst particles in the cyclone separating system is then withdrawn from the reactor vessel 220 through top gas outlet means 256. The recovered hydrocarbon product comprising $C_5+$ olefins and/or aromatics, paraffins and naphthenes is thereafter processed as required to provide a desired gasoline or higher boiling product.

Under optimized process conditions the turbulent bed has a superficial vapor velocity of about 0.3 to 2 meters per second (m/sec). At higher velocities entrainment of fine particles may become excessive and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m$^3$, preferrably about 300 to 500 kg/m$^3$, measured at the bottom of the reaction zone, becoming less dense toward the top of the reaction zone, due to pressure drop and particle size differentiation. The weight hourly space velocity and uniform contact provides a close control of contact time between vapor and solid phases, typically about 3 to 15 seconds.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2, operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime. The reactor can assume any technically feasible configuration, but several important criteria should be considered. The bed of catalyst in the reactor can be at least about 5-20 meters in height, preferably about 9 meters.

The following example tabulates typical FCC light gas oligomerization reactor feed and effluent compositions and shows process conditions for a particular case in which the reactor temperature is controlled at 400° C. The reactor may be heat balanced by controlled preheating the feed to about 135° C. The preferred catalyst is H-ZSM-5 (25 wt. %) with particle distribution as described above for turbulent bed operation.

TABLE

| Composition, wt. % | Gas Feed | Effluent |
|---|---|---|
| H$_2$ | 0.9 | 0.9 |
| C$_1$ | 18.7 | 18.7 |
| C$_3$ | 17.2 | 17.5 |
| C$_2$= | 15.4 | 2.1 |
| C$_3$ | 6.5 | 9.2 |
| C$_3$= | 16.5 | 1.8 |
| iC$_4$ | 3.8 | 7.9 |
| nC$_4$ | 0.8 | 2.7 |
| C$_4$= | 3.9 | 3.1 |
| C$_5$+ | 3.8 | 23.6 |
| N$_2$ | 10.3 | 10.3 |
| CO | 2.2 | 2.2 |
|  | 100 | 100 |

Reactor Conditions

| | |
|---|---|
| Temperature, °C. | 400 |
| Pressure | 1200 kPa |
| Olefin WHSV (based on total cat. wt.) | 0.4 |

While the invention has been described by specific examples and embodiments, there is no intent to limit the inventive concept except as set forth in the following claims.

We claim:

1. A continuous multi-stage catalytic reactor system for converting ethene-rich lower olefinic feedstock to heavier liquid hydrocarbon product, comprising:
   primary stage reactor means for contacting said lower olefinic feedstock at elevated temperature and moderate pressure in a primary stage higher severity reaction zone with shape selective medium pore zeolite oligomerization catalyst to convert at least a portion of the lower olefin to intermediate olefinic hydrocarbons;
   means for cooling primary stage oligomerization reaction effluent from the high severity reaction zone to condense at least a portion of the intermediate hydrocarbons;
   first phase separation means for separating the cooled and partially condensed high severity reactor effluent stream in a primary phase separation zone into a light gas phase stream comprising unreacted light olefin and a condensed liquid intermediate hydrocarbon stream;
   pump means for pressurizing the intermediate liquid stream from the primary stage for a high pressure second stage;
   secondary reactor means for contacting said pressurized intermediate liquid stream with shape selective medium pore zeolite oligomerization catalyst in a secondary stage distillate mode catalytic reaction zone at elevated temperature and high pressure to provide a heavier hydrocarbon effluent stream comprising distillate and lighter hydrocarbons;
   means for flashing and cooling the secondary stage effluent stream;
   second phase separator means for separating and recovering a distillate-rich product stream and a lighter hydrocarbon vapor stream comprising intermediate hydrocarbons, including means for controlling temperature of said second separation zone higher than said primary separation zone to vaporize a major amount of the C$_9$− hydrocarbons in the secondary stage effluent; and
   fluid handling means operatively connected between said primary and secondary stages for recycling at least a portion of the recovered secondary stage vapor stream for combining with primary stage effluent prior to introduction to said first stage separation means.

2. The system of claim 1 including means for maintaining said secondary phase separation means at operating pressure between the primary and secondary stage reactors.

3. The process of claim 1 including means for removing a gas slipstream comprising C$_4$− light gas from said first separation means.

4. The system of claim 1 further including means for recycling a major portion of the primary gas stream to a fixed bed primary stage reaction zone;

5. A two-stage catalytic system for converting ethene-rich lower olefinic feedstock to heavier liquid hydrocarbon product, comprising primary stage reactor means for contacting ethene-rich feedstock at elevated temperature and moderate pressure in a high severity reaction zone with shape selective medium pore zeolite oligomerization catalyst to convert at least a portion of the lower olefinic components to intermediate olefinic hydrocarbons;

first low temperature phase separator means for cooling primary stage oligomerization reaction effluent from the high severity reaction zone to condense at least a portion of the intermediate hydrocarbons and separating the cooled and partially condensed high severity reactor effluent stream in a primary phase separation zone into a light gas phase stream comprising unreacted light olefin and a condensed liquid intermediate hydrocarbon stream;

compressor means for recycling a major portion of the primary gas stream to the primary stage reaction zone;

pump means for pressurizing and passing said intermediate liquid stream to a secondary stage;

secondary stage reactor means for contacting the intermediate liquid stream from the primary stage with shape selective medium pore zeolite oligomerization catalyst in a secondary stage distillate mode catalytic reactor system at elevated temperature and high pressure to provide a heavier hydrocarbon effluent stream comprising distillate and lighter hydrocarbons;

second high temperature phase separator means for flashing and cooling the secondary stage effluent stream in a secondary phase separation zone to recover distillate-rich liquid product stream and lighter hydrocarbon vapor stream comprising intermediate hydrocarbons;

means for recycling at least a portion of the recovered secondary stage vapor stream for combining in the primary stage effluent prior to phase separation; and fractionation means for recovering distillate and gasoline range hydrocarbons from the secondary stage liquid product stream.

* * * * *